US008878919B2

(12) United States Patent
Tsuyuki

(10) Patent No.: US 8,878,919 B2
(45) Date of Patent: Nov. 4, 2014

(54) ENDOSCOPE SYSTEM

(71) Applicant: Olympus Medical Systems Corp., Tokyo (JP)

(72) Inventor: Hiroshi Tsuyuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 9 days.

(21) Appl. No.: 13/856,111

(22) Filed: Apr. 3, 2013

(65) Prior Publication Data

US 2013/0271587 A1 Oct. 17, 2013

Related U.S. Application Data

(63) Continuation of application No. PCT/JP2012/076658, filed on Oct. 16, 2012.

(30) Foreign Application Priority Data

Oct. 27, 2011 (JP) ................................ 2011-236387

(51) Int. Cl.
*H04N 7/18* (2006.01)
*A61B 1/05* (2006.01)
*A61B 1/00* (2006.01)

(52) U.S. Cl.
CPC ............... *H04N 7/181* (2013.01); *A61B 1/051* (2013.01); *A61B 1/00188* (2013.01); *A61B 1/00009* (2013.01); *A61B 1/0005* (2013.01)
USPC .......................................................... 348/65

(58) Field of Classification Search
USPC .............................. 348/61, 65, 71
See application file for complete search history.

(56) References Cited

FOREIGN PATENT DOCUMENTS

| JP | 09-116807 | 5/1997 |
|---|---|---|
| JP | 11-197097 | 7/1999 |
| JP | 11-197098 | 7/1999 |
| JP | 2002-010126 | 1/2002 |
| JP | 2002-209831 | 7/2002 |
| JP | 2003-078802 | 3/2003 |
| JP | 2003-259186 | 9/2003 |
| JP | 2003-290134 | 10/2003 |
| JP | 2004-350070 | 12/2004 |
| JP | 2005-176940 | 7/2005 |
| JP | 2007-313166 | 12/2007 |
| JP | 2011-062378 | 3/2011 |

OTHER PUBLICATIONS

International Search Report, dated Nov. 20. 2012, issued in corresponding International Application No. PCT/JP2012/076658.

*Primary Examiner* — Allen Wong
(74) *Attorney, Agent, or Firm* — Kenyon & Kenyon LLP

(57) ABSTRACT

An endoscope system includes an endoscope objective optical system that acquires two optical images with different focus positions, an image pickup device that picks up the two optical images to acquire two image signals, an image synthesis processing section that makes a comparison in contrast between the two image signals for each spatially identical pixel region and selects a pixel region having relatively higher contrast to thereby synthesize the two image signals into one image, and a focus switchover mechanism that moves a position of a focus switchover lens provided for the endoscope objective optical system and selectively switches a focus of the endoscope objective optical system to one of two observation regions of proximity observation and remote observation, in which the image synthesis processing section synthesizes two images in each of the respective observation regions of the proximity observation and the remote observation.

16 Claims, 8 Drawing Sheets

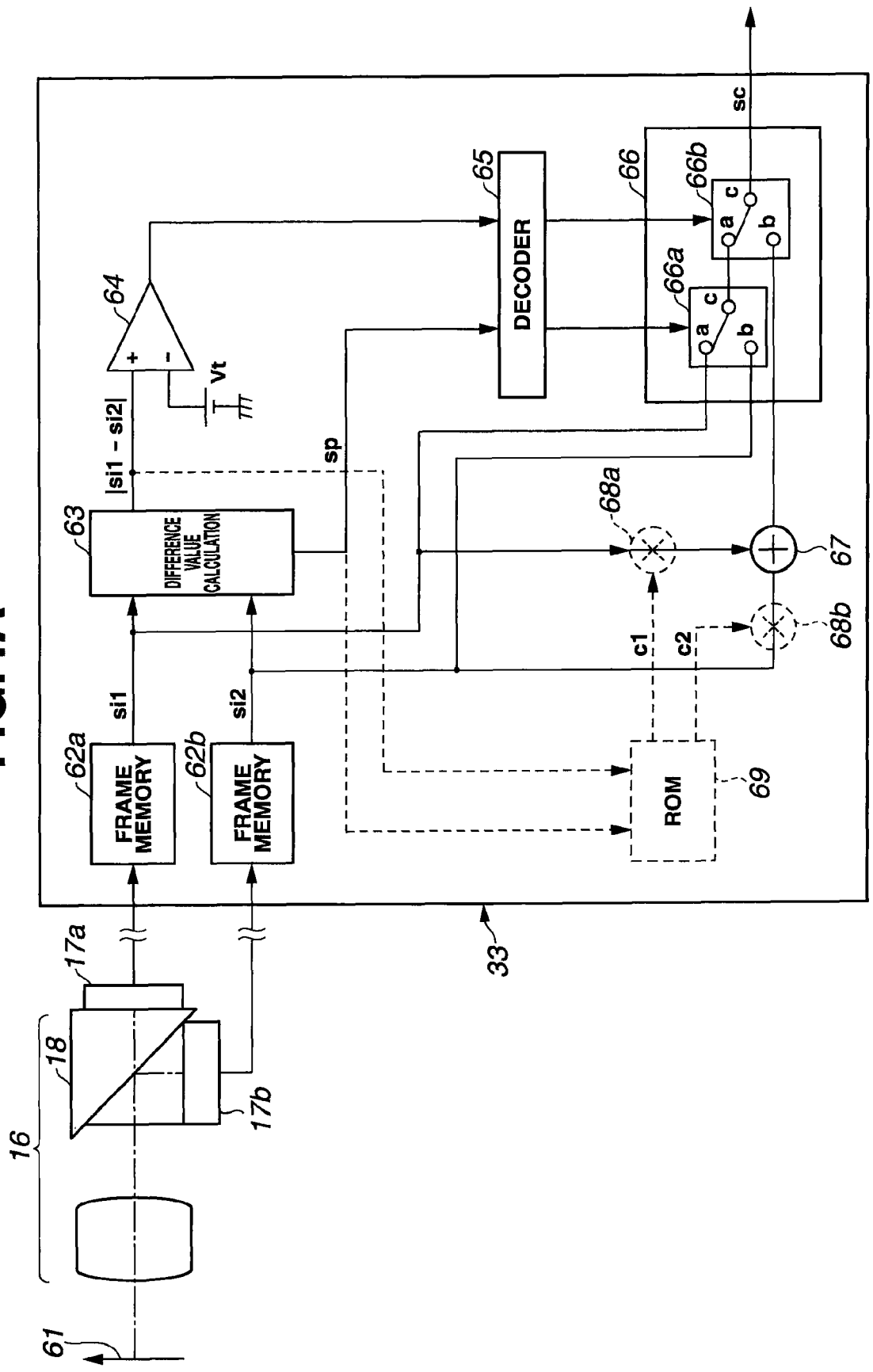

FIG.5
(A)
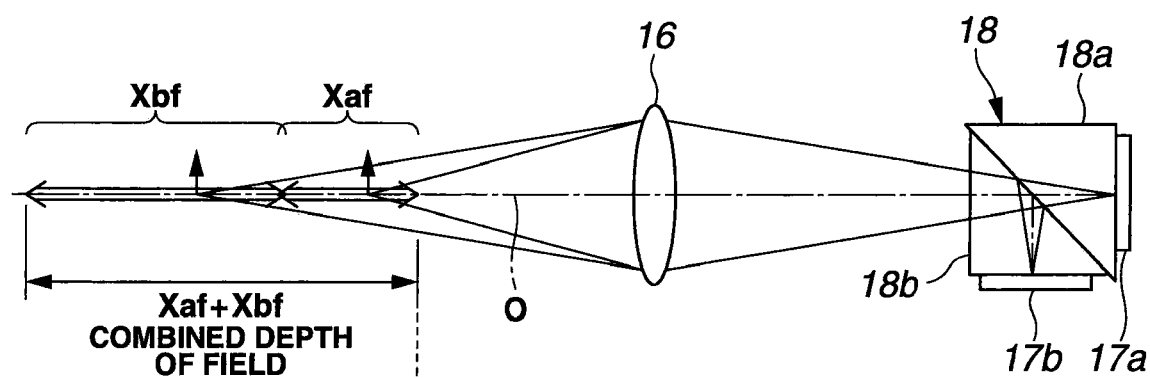
(B)
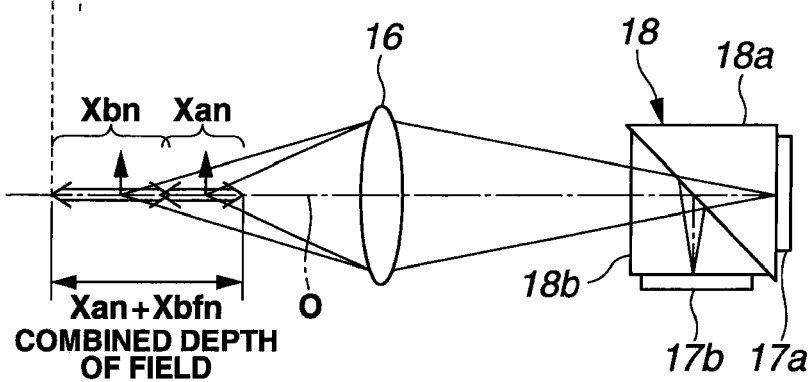

| EMBODIMENT | 2≤Fno.Pix ≤4.5 | Pix (μm) | Fno. | k1 | k2 | DEPTH OF FIELD WITH REMOTE OBSERVATION FOCUS | | | DEPTH OF FIELD WITH PROXIMITY OBSERVATION FOCUS | | | NEAR WIDTH OF DEPTH OF FIELD | IMAGE PICKUP SCHEME | TOTAL NUMBER OF PIXELS |
|---|---|---|---|---|---|---|---|---|---|---|---|---|---|---|
| | | | | | | far1 DEPTH (mm) | far2 DEPTH (mm) | COMBINED FAR DEPTH (mm) | near1 DEPTH (mm) | near2 DEPTH (mm) | COMBINED NEAR DEPTH (mm) | | | |
| FIRST (UPPER LIMIT OF EQUATION 5) | 4.50 | 1.7 | 7.65 | 3.0 | 1.0 | NEAR POINT: 6.54 (MTF: 10.02 %) FAR POINT: 10.45 (MTF: 10.00 %) BST 8.1 mm | NEAR POINT: 10.41 (MTF: 10.00 %) FAR POINT: 128.59 (MTF: 10.00 %) BST 18 mm | 6.54 - 128.59 | NEAR POINT: 3.18 (MTF: 10.01 %) FAR POINT: 4.30 (MTF: 10.01 %) BST 3.5 mm | NEAR POINT: 4.16 (MTF: 10.01 %) FAR POINT: 7.43 (MTF: 10.00 %) BST 5 mm | 3.18 - 7.43 | 4.25 | COMPLEMENTARY COLOR | 1030580 |
| SECOND (LOWER LIMIT OF CONDITIONAL EQUATION 5) | 2.40 | 1.45 | 3.48 | 2.0 | 0.8 | NEAR POINT: 7.03 (MTF: 10.09 %) FAR POINT: 12.92 (MTF: 10.04 %) BST 9.5 mm | NEAR POINT: 12.20 (MTF: 10.39 %) FAR POINT: 46.24 (MTF: 10.00 %) BST 21 mm | 7.03 - 46.24 | NEAR POINT: 3.50 (MTF: 10.08 %) FAR POINT: 4.73 (MTF: 10.01 %) BST 4.2 mm | NEAR POINT: 4.53 (MTF: 10.26 %) FAR POINT: 6.65 (MTF: 10.06 %) BST 5.4 mm | 3.5 - 6.65 | 3.15 | FRAME SEQUENTIAL | 858816 |
| THIRD | 4.20 | 1.1 | 4.62 | 2.8 | 1.0 | NEAR POINT: 7.12 (MTF: 10.04 %) FAR POINT: 12.91 (MTF: 10.03 %) BST 9 mm | NEAR POINT: 12.90 (MTF: 10.14 %) FAR POINT: 59.17 (MTF: 10.00 %) BST 20 mm | 7.12 - 59.17 | NEAR POINT: 4.33 (MTF: 10.01 %) FAR POINT: 6.20 (MTF: 10.01 %) BST 5.1 mm | NEAR POINT: 5.38 (MTF: 10.02 %) FAR POINT: 8.41 (MTF: 10.03 %) BST 6.5 mm | 4.33 - 8.41 | 4.08 | PRIMARY COLOR BAYER | 1512500 |
| FOURTH | 4.20 | 1.45 | 6.09 | 2.8 | 1.0 | NEAR POINT: 8.26 (MTF: 10.06 %) FAR POINT: 14.24 (MTF: 10.02 %) BST 10.6 mm | NEAR POINT: 14.10 (MTF: 10.11 %) FAR POINT: 46.54 (MTF: 10.00 %) BST 22 mm | 8.89 - 46.54 | NEAR POINT: 4.44 (MTF: 10.05 %) FAR POINT: 5.86 (MTF: 10.10 %) BST 5.1 mm | NEAR POINT: 5.78 (MTF: 10.05 %) FAR POINT: 8.38 (MTF: 10.03 %) BST 6.9 mm | 5.1 - 8.38 | 3.28 | PRIMARY COLOR BAYER | 1512500 |
| FIFTH (UPPER LIMIT OF EQUATION 5) | 4.20 | 1.1 | 4.62 | 2.8 | 1.0 | NEAR POINT: 6.73 (MTF: 10.08 %) FAR POINT: 10.78 (MTF: 10.01 %) BST 7.8 mm | NEAR POINT: 10.71 (MTF: 10.07 %) FAR POINT: 104.49 (MTF: 10.00 %) BST 17 mm | 6.73 - 104.49 | NEAR POINT: 3.00 (MTF: 10.02 %) FAR POINT: 3.72 (MTF: 10.01 %) BST 3.3 mm | NEAR POINT: 3.72 (MTF: 10.01 %) FAR POINT: 5.87 (MTF: 10.01 %) BST 4.5 mm | 3 - 5.87 | 2.87 | PRIMARY COLOR BAYER | 1200500 |
| SIXTH | 4.20 | 1.7 | 7.14 | 2.8 | 1.0 | NEAR POINT: 7.41 (MTF: 10.12 %) FAR POINT: 14.05 (MTF: 10.09 %) BST 10 mm | NEAR POINT: 13.80 (MTF: 10.07 %) FAR POINT: 78.67 (MTF: 10.00 %) BST 25 mm | 7.41 - 78.67 | NEAR POINT: 3.53 (MTF: 10.22 %) FAR POINT: 4.87 (MTF: 10.25 %) BST 4.1 mm | NEAR POINT: 4.94 (MTF: 10.11 %) FAR POINT: 7.48 (MTF: 10.09 %) BST 5.9 mm | 3.53 - 7.48 | 3.95 | PRIMARY COLOR BAYER | 1001505 |

(B)

| EMBODIMENT | 2≤Fno.Pix ≤4.5 | Pix (μm) | Fno. | k1 | k2 | DEPTH OF FIELD WITH REMOTE OBSERVATION FOCUS | | | DEPTH OF FIELD WITH PROXIMITY OBSERVATION FOCUS | | | NEAR WIDTH OF DEPTH OF FIELD | IMAGE PICKUP SCHEME | TOTAL NUMBER OF PIXELS |
|---|---|---|---|---|---|---|---|---|---|---|---|---|---|---|
| | | | | | | far1 DEPTH (mm) | far2 DEPTH (mm) | COMBINED FAR DEPTH (mm) | near1 DEPTH (mm) | near2 DEPTH (mm) | COMBINED NEAR DEPTH (mm) | | | |
| SECOND' | 2.70 | 1.45 | 3.92 | 2.0 | 0.9 | NEAR POINT: 6.79 (MTF: 10.05 %) FAR POINT: 12.92 (MTF: 10.03 %) BST 9 mm | NEAR POINT: 12.60 (MTF: 10.10 %) FAR POINT: 81.19 (MTF: 10.12 %) BST 22 mm | 6.79 - 81.19 | NEAR POINT: 3.44 (MTF: 10.07 %) FAR POINT: 4.75 (MTF: 10.12 %) BST 4 mm | NEAR POINT: 4.56 (MTF: 10.08 %) FAR POINT: 7.05 (MTF: 10.04 %) BST 5.5 mm | 3.44 - 7.05 | 3.61 | FRAME SEQUENTIAL | 858816 |
| FIRST' | 4.50 | 1.7 | 7.65 | 3.0 | 1.0 | NEAR POINT: 6.54 (MTF: 10.02 %) FAR POINT: 10.45 (MTF: 10.00 %) BST 8.1 mm | NEAR POINT: 10.41 (MTF: 10.00 %) FAR POINT: 128.59 (MTF: 10.00 %) BST 18 mm | 6.54 - 128.59 | NEAR POINT: 3.18 (MTF: 10.01 %) FAR POINT: 4.30 (MTF: 10.01 %) BST 3.5 mm | NEAR POINT: 4.16 (MTF: 10.01 %) FAR POINT: 7.43 (MTF: 10.00 %) BST 5 mm | 3.18 - 7.43 | 4.25 | COMPLEMENTARY COLOR | 1030580 |

(C)

| EMBODIMENT | 3≤Fno.Pix ≤4.2 | Pix (μm) | Fno. | k1 | k2 | DEPTH OF FIELD WITH REMOTE OBSERVATION FOCUS | | | DEPTH OF FIELD WITH PROXIMITY OBSERVATION FOCUS | | | NEAR WIDTH OF DEPTH OF FIELD | IMAGE PICKUP SCHEME | TOTAL NUMBER OF PIXELS |
|---|---|---|---|---|---|---|---|---|---|---|---|---|---|---|
| | | | | | | far1 DEPTH (mm) | far2 DEPTH (mm) | COMBINED FAR DEPTH (mm) | near1 DEPTH (mm) | near2 DEPTH (mm) | COMBINED NEAR DEPTH (mm) | | | |
| FOURTH' | 2.97 | 1.45 | 4.31 | 2.2 | 0.9 | NEAR POINT: 8.26 (MTF: 10.01 %) FAR POINT: 14.24 (MTF: 10.02 %) BST 10.6 mm | NEAR POINT: 14.10 (MTF: 10.11 %) FAR POINT: 46.54 (MTF: 10.00 %) BST 22 mm | 8.89 - 46.54 | NEAR POINT: 4.44 (MTF: 10.11 %) FAR POINT: 5.86 (MTF: 10.02 %) BST 5.1 mm | NEAR POINT: 5.78 (MTF: 10.05 %) FAR POINT: 8.38 (MTF: 10.10 %) BST 6.9 mm | 5.1 - 8.38 | 3.28 | PRIMARY COLOR BAYER | 1512500 |
| THIRD' | 4.20 | 1.1 | 4.52 | 2.8 | 1.0 | NEAR POINT: 7.99 (MTF: 10.04 %) FAR POINT: 13.52 (MTF: 10.01 %) BST 9.7 mm | NEAR POINT: 13.50 (MTF: 10.04 %) FAR POINT: 61.62 (MTF: 10.00 %) BST 20.5 mm | 7.99 - 61.62 | NEAR POINT: 4.05 (MTF: 10.02 %) FAR POINT: 5.70 (MTF: 10.12 %) BST 5.4 mm | NEAR POINT: 5.22 (MTF: 10.01 %) FAR POINT: 8.12 (MTF: 10.09 %) BST 7.5 mm | 5.01 - 7.9 | 4.07 | PRIMARY COLOR BAYER | 1512500 |

ENDOSCOPE SYSTEM

CROSS REFERENCE TO RELATED APPLICATION

This application is a continuation application of PCT/JP2012/076658 filed on Oct. 16, 2012 and claims benefit of Japanese Application No. 2011-236387 filed in Japan on Oct. 27, 2011, the entire contents of which are incorporated herein by this reference.

BACKGROUND OF THE INVENTION

1. Field of the Invention

The present invention relates to an endoscope system that forms an image of light from an objective optical system provided for an endoscope on two image pickup devices.

2. Description of the Related Art

In recent years, endoscope systems using an endoscope equipped with an image pickup device are widely used in medical and industrial fields.

Furthermore, since a depth of field generally becomes narrower as the number of pixels of the image pickup device increases, there are various proposals relating to this problem.

As a first conventional example, Japanese Patent Application Laid-Open Publication No. 9-116807 discloses an image pickup apparatus that includes an image pickup device arranged at a focus position and at least one image pickup device arranged at a position shifted from the focus position within a range in which a range of depth of field thereof has an area common to a range of depth of field of the image pickup device arranged at the focus position, extracts a high-frequency signal component from an output signal of the at least one image pickup device and performs signal processing of adding the high-frequency signal component to an output signal of the image pickup device arranged at the focus position.

Furthermore, as a second conventional example, Japanese Patent Application Laid-Open Publication No. 2003-78802 discloses an image pickup apparatus including an image pickup device drive apparatus that divides an optical path of light that passes through an image pickup lens that picks up images of objects located at different distances into a plurality of optical paths using optical path dividing means, arranges image pickup devices having different focus positions in the divided respective optical paths and moves the respective image pickup devices along an optical axis direction, a calculation processing apparatus that determines positions on the optical axis of the respective image pickup devices in accordance with an inputted lens parameter of the image pickup lens, and an image synthesis apparatus that synthesizes video signals outputted from the respective image pickup devices.

As a third conventional example, Japanese Patent Application Laid-Open Publication No. 2007-313166 discloses an endoscope that includes a focus adjustment mechanism for capturing a high quality image and two-plate image pickup units arranged by being shifted by approximately ½ pitch pixel in horizontal and vertical directions, in which the vertical direction pixel pitch of the image pickup device and an F number of the objective optical system are set so as to satisfy a predetermined condition.

SUMMARY OF THE INVENTION

An endoscope system according to an aspect of the present invention includes an endoscope objective optical system that acquires two optical images with different focus positions from an identical object, an image pickup device that picks up the two optical images to acquire two image signals, an image synthesis processing section that makes a comparison in contrast between the two image signals for each spatially identical pixel region, and selects a pixel region having relatively higher contrast to thereby synthesize two image signals into one image, and a focus switchover mechanism that moves a position of a focus switchover lens provided for the endoscope objective optical system and selectively switches a focus of the endoscope objective optical system to one of two observation regions of proximity observation and remote observation, in which the image synthesis processing section synthesizes two images in each of the respective observation regions of the proximity observation and the remote observation.

BRIEF DESCRIPTION OF THE DRAWINGS

FIG. 4A is a diagram illustrating a configuration of an image synthesis processing section;

FIG. 5 is a diagram illustrating operation of expanding the depth of field through focus switchover of the objective optical system using a focus lens;

FIG. 6 is a diagram illustrating numerical value data of depth of field or the like according to the first embodiment or the like in a table format;

DETAILED DESCRIPTION OF THE PREFERRED EMBODIMENTS

Hereinafter, embodiments of the present invention will be described with reference to the accompanying drawings.
(First Embodiment)

Figure 1:
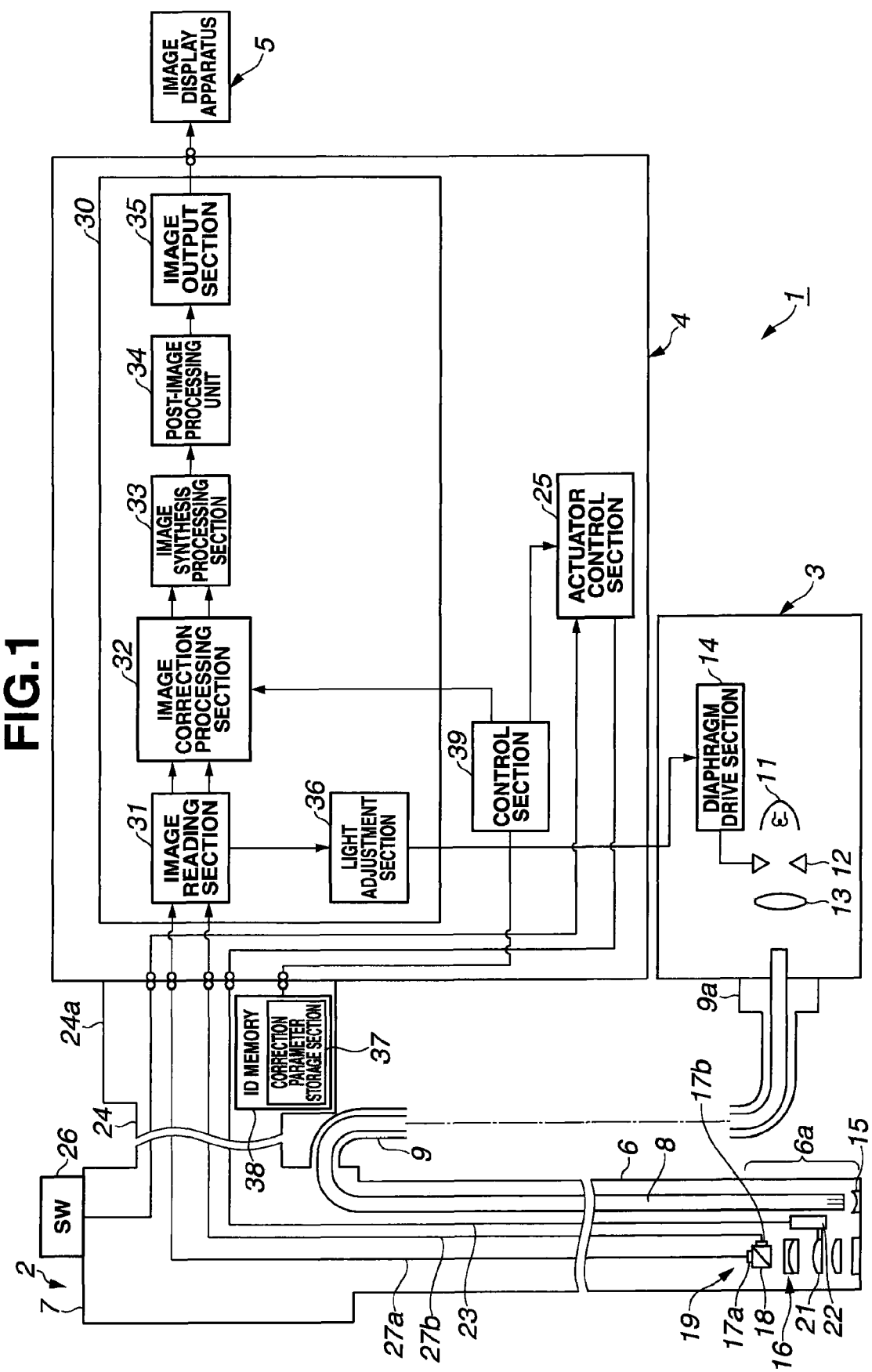
FIG. 1 is a diagram illustrating an overall configuration of an endoscope system according to a first embodiment of the present invention.

As shown in FIG. 1, an endoscope system 1 according to a first embodiment of the present invention includes an endoscope 2 that is inserted into a subject, a light source apparatus 3 that supplies illuminating light to the endoscope 2, a processor apparatus 4 as an image processing apparatus that performs image processing on image pickup means provided on the endoscope 2, and an image display apparatus 5 that displays an image signal generated by the processor apparatus 4 as an endoscope image.

The endoscope 2 includes an elongated insertion portion 6 inserted into the subject, and an operation section 7 provided at a rear end of the insertion portion 6, and a light guide connector 9a at an end of a first cable 9 through which a light guide 8 that extends from the operation section 7 and transmits illuminating light is inserted is detachably connected to the light source apparatus 3.

The light source apparatus 3 incorporates a lamp 11 such as a xenon lamp as a light source. Note that the light source is not limited to the lamp 11 such as xenon lamp, but a light-emitting diode (abbreviated as "LED") may also be used. White color light generated by the lamp 11 is adjusted in its passing light quantity by a diaphragm 12, and then condensed by a condenser lens 13 and made incident on (supplied to) an incident end face of the light guide 8. Note that an aperture value of the diaphragm 12 can be changed by a diaphragm drive section 14.

The light guide 8 transmits the illuminating light made incident on an incident end face and allows it to exit from a front end face disposed inside an illuminating window of a distal end portion 6a of the insertion portion 6. An illumination lens 15 is arranged in front of this front end face and the illumination lens 15 spreads the light exited from the front end face of the light guide 8 through the illuminating window to illuminate a site to be observed in the subject.

The illuminated site to be observed is caused by an endoscope objective optical system (hereinafter, simply abbreviated as "objective optical system") 16 attached to the observation window provided adjacent to the illuminating window to form an optical image on two image pickup devices 17a and 17b arranged at the rear thereof.

Figure 2A:
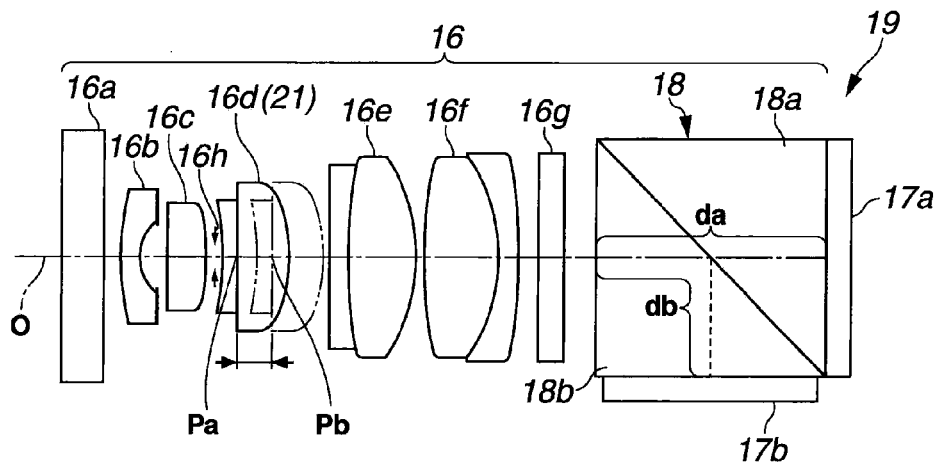
FIG. 2A is a diagram illustrating a configuration of an objective optical system and an image pickup device according to the first embodiment.

As shown in FIG. 2A, the objective optical system 16 according to the present embodiment includes a plurality of optical elements 16a to 16h arranged along an optical axis O thereof, and is also provided with a prism 18 as an optical element arranged on the optical axis O between the rear side of the optical element 16g and the front side of the two image pickup devices 17a and 17b to divide the optical image into two optical images. Note that the brightness diaphragm 16h is arranged between the optical elements 16c and 16d.

This prism 18 is formed of, for example, right triangle prism elements 18a and 18b disposed so that both inclined surfaces thereof contact each other, and one image pickup device 17a is attached to the vicinity of an end face of the prism element 18a (so as to face the end face) and the other image pickup device 17b is attached to the vicinity of an end face of the prism element 18b (so as to face the end face). Note that it is preferable to use the image pickup device 17a and the image pickup device 17b having the same or matched characteristics.

The prism 18 divides light made incident through the optical elements 16a to 16h into, for example, reflected light and transmitted light of equal quantity to thereby form two optical images: an optical image on the transmitted light side and an optical image on the reflected light side. The image pickup device 17a receives and photoelectrically converts the optical image on the transmitted light side, and the image pickup device 17b receives and photoelectrically converts the optical image on the reflected light side.

In the present embodiment, the image pickup devices 17a and 17b are attached to the vicinity of the end faces of the prism elements 18a and 18b such that their focus positions differ from each other. A setting is made such that an optical path length db on the reflected light side is shorter (smaller) than an optical path length da up to the image pickup device 17a on the transmitted light side in the prism 18. Regarding both image pickup devices 17a and 17b, the image pickup device 17a has a focus position relatively shifted (displaced) to a near point side with respect to the image pickup device 17b and the image pickup device 17b has a focus position relatively shifted to a far point side with respect to the image pickup device 17a.

Note that it may also be possible to cause the refractive index of the prism element 18a to differ from that of the prism element 18b, thereby change the optical path lengths up to the image pickup devices 17a and 17b and relatively shift the focus positions of both image pickup devices 17a and 17b.

Figure 2B:
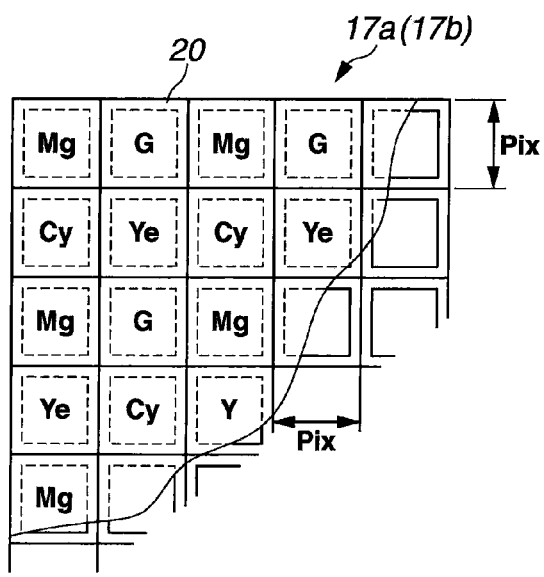
FIG. 2B is a diagram illustrating a complementary color-based color separation filter attached to the image pickup surface of the image pickup device.

Furthermore, complementary color-based color separation filters 20 are attached to the respective image pickup surfaces of both image pickup devices 17a and 17b as shown in FIG. 2B. More specifically, the color separation filters 20 made up of four color filter elements of magenta Mg, green G, cyan Cy and yellow Y arranged immediately before the respective pixels at a predetermined pixel pitch (also referred to as "pixel size") Pix are regularly arrayed in the horizontal direction and the vertical direction on the image pickup surfaces.

Mg and G are alternately arranged in the horizontal direction and arranged at 2-pixel periods in the vertical direction. On the other hand, Cy and Ye are alternately arranged in the horizontal direction as in the case of Mg and G, but arranged in the vertical direction such that one is switched to the other at pixel positions at 2-pixel periods.

Note that when primary color filters are represented by R, G and B, as the functions of color transmission characteristics, there are relationships such as Mg=R+B, Cy=G+B and Ye=R+G.

The above objective optical system 16 and the two image pickup devices 17a and 17b constitute an image pickup unit 19 that acquires two optical images and acquires two images by photoelectrically converting the two optical images.

Furthermore, the present embodiment provides a focus switchover mechanism so that the objective optical system 16 may selectively achieve focus on two observation regions of remote observation and proximity observation. More specifically, the objective optical system 16 has a focus lens 21 which is movable to two positions Pa and Pb (see FIG. 2A) in the direction of the optical axis O thereof, and this focus lens 21 is driven by an actuator 22 that makes up the focus switchover mechanism to move from one position to the other or vice versa between the two positions Pa and Pb.

In the configuration example in FIG. 2A, the focus lens 21 is made up of, for example, a cemented lens, that is, a concave lens and a convex lens bonded together so as to have positive power, and this focus lens 21 is arranged between a brightness diaphragm denoted by reference numeral 16d on the front side (object side) and the cemented lens 16f, and is selectively set to two positions Pa and Pb: position Pa immediately after the brightness diaphragm 16d and position Pb immediately before the cemented lens 16f.

Note that as will be described later using FIG. 5, in a condition with the focus lens 21 being set at the position Pa on the front side (object side), a setting is made such that the object in an observation region when remote observation is performed is brought into focus using the image pickup devices 17a and 17b.

On the other hand, in a condition with the focus lens 21 being set at the position Pb on the rear side, a setting is made such that the object in an observation region when proximity observation is performed is brought into focus using the image pickup devices 17a and 17b.

Focus positions of both image pickup devices 17a and 17b are shifted from each other and, as will be described later, the respective focus positions are set so as to overlap with each other within a range of each depth of field where an MTF (modulation transfer function) reaches a predetermined value or above, and therefore by synthesizing two images acquired by both image pickup devices 17a and 17b, it is possible to obtain a synthesized image having a wide depth of field.

As shown in FIG. 1, the actuator 22 is connected to a signal line 23 inserted through the insertion portion 6 and the signal line 23 is further inserted through a second cable 24 that extends from the operation section 7. A signal connector 24a at an end of the second cable 24 is detachably connected to the processor apparatus 4 and the signal line 23 is connected to an actuator control section 25 provided in the processor apparatus 4.

The actuator control section 25 also receives a switchover operation signal from a switchover operation switch 26 provided, for example, in the operation section 7 of the endoscope 2. The actuator control section 25 applies a drive signal for electrically driving the actuator 22 in accordance with operation of the switchover operation switch 26 to move the focus lens 21.

Note that switchover operation means for generating a switchover operation signal is not limited to the switchover operation switch 26, but may also be a switchover operation lever or the like. The above-described focus lens 21, actuator 22 and actuator control section 25 form a focus switchover mechanism.

The image pickup devices 17a and 17b are connected to signal lines 27a and 27b which are inserted through the insertion portion 6, the operation section 7 and the second cable 24, and when the signal connector 24a is connected to the processor apparatus 4, the image pickup devices 17a and 17b are connected to an image processor 30 as an image processing unit provided in the processor apparatus 4.

This image processor 30 includes an image reading section 31 that reads respective image signals (simply abbreviated as "images") picked up by the two image pickup devices 17a and 17b with different focus positions and photoelectrically converted, an image correction processing section 32 that performs image correction on the two images read by this image reading section 31 and an image synthesis processing section 33 that performs image synthesis processing of synthesizing the two corrected images.

The image correction processing section 32 performs image processing on the two images photoelectrically converted by the image pickup devices 17a and 17b so as to cancel a relative magnification difference, a position difference, a rotation difference and a brightness difference between images formed on the image pickup surfaces of the two image pickup devices 17a and 17b respectively.

When an image is divided into two portions and the respective images are formed on different image pickup devices, the following geometric differences may occur.

The respective images formed on the image pickup surfaces of the two image pickup devices 17a and 17b may be subject to a relative magnification difference, a position difference, a rotation direction difference or a brightness difference due to a sensitivity difference or the like between the two image pickup devices 17a and 17b. It is difficult to completely eliminate these differences at the time of production or the like. However, when the amount of these differences increases, the synthesized image may become a hybrid image or an unnatural brightness variation may occur. For this reason, in the present embodiment, the image correction processing section 32 corrects the aforementioned geometric difference and brightness difference.

When correcting the relative brightness difference, the image correction processing section 32 performs correction using one of the two images with lower luminance or one of the two images with relatively low luminance at the same position as a reference.

A difference in brightness (luminance value) may occur when an image of the same object is picked up due to a sensitivity difference in the respective image pickup chips of the two image pickup devices 17a and 17b or an on-chip lens manufacturing error or the like.

In such a case, brightness is corrected so as to match the relatively darker one, that is, a luminance signal (e.g., G signal) with lower intensity (signal level). To the contrary of this correction, if the brightness is corrected so as to match the brighter one, even a noise component contained in the image needs to be amplified, resulting in a synthesized image with a degraded S/N.

As described above, performing brightness correction so as to lower (attenuate) the gain to adjust the gain corresponding to higher luminance to the gain corresponding to lower luminance using the gain corresponding to lower luminance as a reference, it is possible to prevent image quality of a synthesized image from degrading due to S/N degradation.

The image synthesis processing section 33 compares the two images regarding the contrast in spatially the same pixel region, selects a pixel region with relatively high contrast, and thereby generates a synthesized image as one image which is synthesized from the two images. Note that when the difference in contrast between the two images is small, a synthesized image is generated through synthesized image processing of assigning predetermined weights to the respective images and adding up the weighted images.

FIG. 4A illustrates a configuration example of the image synthesis processing section 33 that performs such image synthesis processing. The objective optical system 16 forms two optical images of an identical object 61 on the image pickup surfaces of the two CCDs 17a and 17b having different focus positions. The first and second image data which have been photoelectrically converted by the CCDs 17a and 17b and have passed through the image correction processing section 32 or the like (based on the image pickups of the CCDs 17a and 17b, respectively) are stored in two frame memories 62a and 62b in the image synthesis processing section 33 in pixel units.

Note that when one-frame's worth of image data corresponding to the same region is stored in the two frame memories 62a and 62b, the first image data and the second image data corresponding to the same region are stored in a memory cell of the same address.

Furthermore, a signal having a brightness value or luminance level corresponding to a contrast value in the case of one color signal component will be described below and other color signal components are also assumed to be subjected to similar processing. Note that it may also be possible to generate a publicly known luminance signal from R, G and B color components and perform similar processing based on the contrast comparison result of the two luminance signals.

Respective signals si1 and si2 of the first image and the second image simultaneously read from the two frame memories 62a and 62b by specification of an identical address are inputted to a difference value calculation circuit 63 made up of a differential amplifier or the like, and the difference value calculation circuit 63 calculates a difference value between both signals si1 and si2 by, for example, subtracting the brightness value of the second image from the brightness value of the first image. Furthermore, the difference value calculation circuit 63 also determines, based on the positive or negative polarity of the difference value, whether the luminance level of any one image is higher (greater) than the other and outputs a binary value signal sp. For example, when the polarity is positive, si1>si2, and when the polarity is negative, si1<si2.

The absolute value |si1−si2| of the difference value calculated by the difference value calculation circuit 63 is inputted to a comparison circuit 64 and the comparison circuit determines whether the absolute value |si1−si2| of the difference value is equal to or greater than a threshold Vt. The comparison circuit 64 outputs a binary signal: an H level when the absolute value |si1−si2| of the difference value is equal to or greater than the threshold Vt and an L level when the absolute value |si1−si2| of the difference value is less than the threshold Vt. The binary signal of the comparison circuit 64 and the binary signal sp corresponding to the polarity from the difference value calculation circuit 63 are inputted to a decoder 65 and the decoder 65 controls switching between two switching circuits 66a and 66b that constitute a selection circuit 66 from the two binary signals.

The signals si1 and si2 are inputted to contacts a and b of the switching circuit 66a respectively, a signal passing through a common contact c of the switching circuit 66a and a signal from an adder 67 are inputted to contacts a and b of the switching circuit 66b, and a combined signal sc subjected to image synthesis processing is outputted from the common contact c of the switching circuit 66b.

The adder 67 adds up the signals si1 and si2 and outputs the addition result to the contact b of the switching circuit 66b.

The decoder 65 selects the contact a of the switching circuit 66b when the absolute value |si1−si2| of the difference value is equal to or greater than the threshold Vt and selects the contact b of the switching circuit 66b when the absolute value |si1−si2| of the difference value is less than the threshold Vt. Furthermore, the decoder 65 selects the contact a or b of the switching circuit 66a in accordance with the binary signal sp of the polarity when the absolute value |si1−si2| of the difference value is equal to or greater than the threshold Vt. More specifically, the decoder 65 selects the signal si1 when the binary signal sp is H level (selection state shown by a solid line in FIG. 4A) and selects the signal si2 when the binary signal is L level. That is, the switching circuit 66a selects an image portion with higher contrast when the contrast difference is equal to or greater than a predetermined value. On the other hand, when the contrast difference is small, the switching circuit 66a adds up the two signals si1 and si2 or the like and outputs the addition result as a combined signal.

Operation in this case will be as follows. The difference value calculation circuit 62 calculates a difference value between the two signals si1 and si2. When the absolute value |si1−si2| of the difference value is equal to or greater than the threshold Vt, the switching circuit 66a selects the signal with a higher luminance level and outputs the signal via the switching circuit 66b as a combined signal sc.

On the other hand, when the absolute value |si1−si2| of the difference value is less than the threshold Vt, the switching circuit 66b selects the signal of the addition result of the adder 67 and outputs this signal as the combined signal sc.

Note that when the absolute value |si1−si2| of the difference value is less than threshold Vt, instead of adding up the signals si1 and si2 to generate the combined signal sc, the signals si1 and si2 may be weighted to generate the combined signal sc as follows. As shown by a dotted line in FIG. 4A, multipliers 68a and 68b are arranged on two input sides of the adder 67, and the multipliers 68a and 68b multiply the signals si1 and si2 by weighting factors c1 and c2 respectively outputted from a ROM 69 and output the respective weighted signals to the adder 67.

Note that the ROM 69 stores the weighting factors c1 and c2 preset in accordance with the difference value and the ROM 69 outputs the weighting factors c1 and c2 by which the signals si1 and si2 are multiplied respectively according to the absolute value |si1−si2| of the difference value and the binary signal sp.

When the difference value is 0, the weighting factors c1 and c2 stored in the ROM 69 become c1=c2=1. Furthermore, the weighting factors c1 and c2 stored in the ROM 69 are set so that for a greater absolute value |si1−si2| of the difference value, the weighting factor corresponding to the signal with a higher luminance level becomes greater than 1 and the weighting factor corresponding to the other signal becomes smaller than 1. The adder 67 then adds up the signals si1 and si2 multiplied by the weighting factors c1 and c2 respectively and outputs the addition result as the combined signal sc.

The above-described image processor 30 includes a post-image processing unit 34 that performs post-image processing such as contour emphasis and gamma correction on the one image synthesized by the image synthesis processing section 33 and an image output section 35 that outputs the image subjected to the post-image processing, and the image outputted from the image output section 35 is outputted to the image display apparatus 5.

Furthermore, this image processor 30 includes a light adjustment section 36 that generates a light adjustment signal for adjusting the brightness to reference brightness from the image read from the image reading section 31, and outputs the light adjustment signal generated by the light adjustment section 36 to the diaphragm drive section 14 of the light source apparatus 3. The diaphragm drive section 14 adjusts the aperture value of the diaphragm 12 so as to maintain the reference brightness according to the light adjustment signal.

Furthermore, the present embodiment provides a correction parameter storage section 37 that stores (information on) correction parameters used for the image correction processing section 32 to correct an image.

Each endoscope 2 includes an ID memory 38 that stores endoscope identification information (endoscope ID) which is specific to the endoscope 2, and when there are specific correction parameters to be corrected in the endoscope 2, the endoscope 2 is provided with the correction parameter storage section 37 that stores correction parameters corresponding to the endoscope 2.

In the configuration example shown in FIG. 1, the correction parameter storage section 37 that stores correction parameters is provided, for example, in the ID memory 38 in the endoscope 2.

Note that when there is no specific correction parameter to be corrected, the correction parameter storage section 37 need not be provided. Furthermore, without being limited to the case where the correction parameter storage section 37 is provided inside the ID memory 38, the correction parameter storage section 37 may be provided in a memory different from the ID memory 38.

A control section 39 of the processor 30 identifies the presence or absence of correction using the endoscope ID provided on the endoscope 2 side, reads the correction parameter from the correction parameter storage section 37 in the ID memory 38 stored on the endoscope 2 side when correction is present and sends this correction parameter to the image correction processing section 32.

The image correction processing section 32 performs image correction corresponding to the image pickup unit 19 mounted on each endoscope 2 based on the above-described correction parameter transferred from the control section 39.

Furthermore, the image correction processing section 32 uses the correction parameter to perform correction of an image such as correction of the aforementioned magnification difference and correction of the position difference, using one of the two images as a reference image.

For example, when there is a magnification difference between the two images, this may be attributable to the specification of the objective optical system 16.

When an attempt is made to make the size of the objective optical system 16 relatively small, such a design may be adopted that telecentricity is lost and light beams diagonally impinge upon the image pickup devices 17a and 17b. For example, such a design is adopted that the angle of incidence is negative when it is assumed that the angle formed with the optical axis is the angle of incidence, clockwise is positive and counterclockwise is negative.

When the focus position is shifted in such an objective optical system whose telecentricity is lost, a magnification difference may occur between two images.

With such a design specification, the system may be designed so as to store the amount of shift in the correction parameter storage section 37, recognize the endoscope 2 when the target endoscope 2 is connected to the processor apparatus 4, invoke the corresponding parameter from the correction parameter storage section 37 and perform correction.

Furthermore, when the image pickup unit 19 is assembled, relative pixel positions of the two images may be shifted minutely. In this case, the amount of shift at the time of manufacture may be stored in the correction parameter storage section 37 so that the image correction processing section 32 corrects the shift.

Regarding positional shift correction, processing of correcting reading positions of the two images is performed so that relative positions of the image picked up by the image pickup device 17a and the image picked up by the image pickup device 17b match, the position shift is corrected and the images are then outputted to the image synthesis processing section 33.

Note that instead of performing correction using a preset correction parameter in the present embodiment, correction may also be performed using an adjustment reference chart provided separately when the endoscope is used. For example, a reference chart may be placed at a desired position of the distal end portion 6a of the endoscope 2, the image correction processing section 32 may read shifts of two images relative to the reference chart and correct the shifts.

Furthermore, even when the position to be driven of the focus lens 21 that constitutes the objective optical system 16 mounted on each endoscope 2 varies, the control section 39 sends information on the position to be driven and even when the type of the endoscope 2 varies, the actuator control section 25 performs control of appropriately driving the actuator 22.

Note that the actuator control section 25 may acquire an ID without through the medium of the control section 39 and perform control even if the type of the endoscope 2 is different, so as to appropriately drive the actuator 22.

Furthermore, the definition of the depth of field in the present specification will be described below with reference to FIG. 3 or the like.

Figure 3:
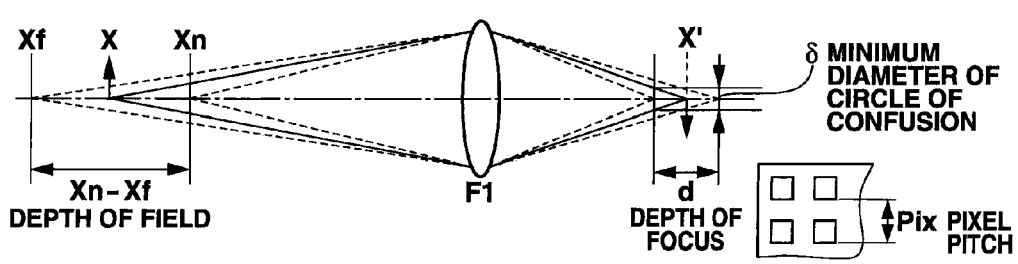
FIG. 3 is a diagram illustrating a depth of field.

FIG. 3 is a diagram illustrating a geometro-optically determined depth of field.

In a general endoscope, using an objective optical system (whose focal length is assumed to be Fl) when the best distance is assumed to be X, a case will be assumed where an image pickup device having a pixel pitch Pix shown in FIG. 3 is arranged at an image surface position X'. When an object is brought closer to Xn (from X) under a condition that the image pickup device is fixed, the image surface position Xn' at the time of approach is shifted from the image pickup surface position of the image pickup device.

In this case, when the maximum circle of confusion that can be considered to be in focus is assumed to be a permissible circle of confusion and the diameter of the circle is assumed to be δ, if the diameter of the circle of confusion on the image pickup surface of the image pickup device can be recognized to be smaller than δ, an object image from X to Xn can be considered to be in focus.

That is, the range until the diameter of the circle of confusion matches δ can be defined as the depth of field on the near point side.

In this case, from Newton's image forming equation, the following equation holds true.

$$1/Xn - 1/X = \delta Fno/Fl^2 \quad (1)$$

Assuming a case where the object is moved (from X) to Xf on the far point side, the equation of the depth of field on the far point side can be likewise defined as follows:

$$1/X - 1/Xf = \delta Fno/Fl^2 \quad (2)$$

If equation (1) and equation (2) are combined, $$1/Xn - 1/Xf = 2\delta Fno/Fl^2 \quad (3)$$

The depth of field corresponding to the depth of focus d becomes Xn-Xf.

Here, as described above, it is assumed that the best distance is X, the distance to the near point of the depth of field is Xn, the distance to the far point of the depth of field is Xf, the diameter of the permissible circle of confusion is δ, the focal length of the objective optical system is Fl, and the effective F number of the objective optical system is Fno.

The above equations are general geometro-optically determined definitions of the depth of field.

In the case of the geometro-optically determined depth of field, the present embodiment can expand the depth of field using a synthesized image, and can also expand the depth of field using a synthesized image even when influences of diffraction cannot be ignored.

When image pickup devices are further miniaturized and implemented with a higher number of pixels, it is generally known that wave-optic effects cannot be ignored when a depth of field is defined. This is because at a focal position, a spot size expands from a geometro-optically defined spot size under influences of diffraction and a deviation from the geometro-optically calculated depth of field is generated. Therefore, diffraction has a non-negligible effect on the endoscope 2 like the present embodiment mounted with a multipixel image pickup device for which narrowing is likely to be performed up to an effective F number Fno close to a diffraction limit. Note that as in the case of the image pickup device shown in FIG. 3, the image pickup devices 17a and 17b of the present embodiment have pixels regularly arranged in the horizontal direction and the vertical direction at the same pixel pitch Pix.

In this case, when an evaluation spatial frequency on the image surface is assumed to be Fi, $$Fi = 1/k1 \cdot Pix \quad (4)$$

If a defocus MTF (modulation transfer function) at Fi is approximately 10%, blur in the image cannot be recognized in objective evaluation and the image can be determined "visible."

In other words, a defocus position at which the MTF becomes approximately 10% can be considered as an end of depth.

The present specification defines the end of depth of field to be 10% of MTF evaluated with an evaluation spatial frequency when a wave-optical end of depth of field is assumed to be Fi=1/k1·Pix.

Furthermore, in the present embodiment, the image pickup unit 19 using the aforementioned image pickup devices 17a and 17b is set so as to obtain characteristics shown in a table in FIG. 6.

FIG. 6 shows numerical value data of Fno/Pix, Pix, Fno, k1, k2, far1 depth (depth of field by the image pickup device 17a during remote observation), far2 depth (depth of field by the image pickup device 17b during remote observation), combined far depth (depth of field of synthesized image during remote observation), near1 depth (depth of field by the image pickup device 17a during proximity observation), near2 depth (depth of field by the image pickup device 17b during proximity observation), combined near depth (depth of field (range) of synthesized image during proximity observation), Near width of depth of field (width of depth of field from combined near depth near point end to combined near depth far point end), image pickup scheme and total number of pixels (total number of pixels of image pickup device). Furthermore, BST indicates the best distance as a distance of an object when MTF becomes maximum.

An overview of this is shown below. As the image pickup devices 17a and 17b, a complementary color-based solid image pickup device is adopted which has million pixels (1030580 pixels) with a pixel size of 1.7 μm.

Furthermore, the present embodiment has the following settings for light having wavelength λ=0.5461 μm: pixel size Pix in the vertical direction of the two image pickup devices 17a and 17b is 1.70 μm, resolution coefficient k1 is 3.00, F value margin k2 is 1.00, effective F number Fno of the objective optical system 16 is 7.65 as correction parameters.

That is,

| | |
|---|---|
| λ | 0.5461 |
| Pix | 1.70 |
| KI | 3.00 |
| k2 | 1.00 |
| Fno | 7.65 |

The image pickup unit 19 of the present embodiment is set so as to satisfy the following condition.

$$2.4 \leq Fno/Pix \leq 4.5 \tag{5}$$

The condition in expression (5) is attributable to the following reason.

It is known that light that passes through the lens that constitutes the objective optical system 16 is affected by diffraction when an image thereof is formed. The greater the effective F number Fno of the objective optical system 16, the greater a point image becomes under the influence of diffraction, and when the size of the point image exceeds a certain limit, details of the object look blurred even if the object is brought into focus.

This limit is defined by Rayleigh as a limit distance within which two point images that come closer to each other are identifiable as separate images, and if it is assumed that λ is the wavelength of light and the effective F number is represented by Fno, the limit is expressed as 1.22·λ·Fno. The distance between two point images at a separation limit, that is, resolution R is expressed as:

$$R = 1.22 \cdot \lambda \cdot Fno \tag{6}$$

On the other hand, when an image is picked up using a charge coupled device (abbreviated as "CCD") or CMOS sensor as an image pickup device, the limit resolution is determined based on a sampling theory. When the pixel size in the vertical direction of the image pickup device is assumed to be Pix, $$R = 2 \cdot Pix \tag{7}$$

Since the resolution R is affected by an interpolation method for the adopted image pickup scheme or characteristics of the electric system, the resolution R is expressed using an arbitrary coefficient k1 as follows:

$$R = k1 \cdot Pix \tag{8}$$

Since the performance of the image pickup device needs to be fully extracted, the coefficient k1 is generally set to on the order of $2 \leq k1 \leq 3$.

From equations (6) and (8), $$k1 \cdot Pix = 1.22 \cdot \lambda \cdot Fno \tag{9}$$

Furthermore, the effective F number Fno set in the objective optical system 16 needs to have a certain degree of allowance in consideration of manufacturing variations or the like to allow the objective optical system 16 to fully display its optical performance.

Therefore, the effective F number Fno defined by the Rayleigh resolution limit equation is actually set in consideration of an arbitrary coefficient k2. That is, $$k1 \cdot Pix = 1.22 \cdot \lambda \cdot Fno \cdot k2 \tag{10}$$

When the size of the objective optical system 16 and balance with the depth of field are taken into consideration, a reasonable range of the coefficient k2 is on the order of $0.7 \leq k2 \leq 1$.

However, when priority is given to the expansion of the depth of field by admitting a certain degree of deterioration in resolution based on the premise of taking advantage of the performance of the image pickup device, the coefficient k2 may also be set to on the order of $0.7 \leq k2 \leq 1.2$.

From equations (9) and (10), the effective F number Fno of the objective optical system 16 to be set is:

$$Fno = Fno^* k2 = (1/1.22 \cdot \lambda) \cdot Pix \cdot k1 \tag{11}$$

Here, if equation (11) is expressed by a relationship between the effective F number Fno and the pixel size Pix, it can be expressed by equation (12) below.

$$Fno/Pix = (1/1.22 \cdot \lambda) \cdot k1 \cdot k2 \tag{12}$$

An endoscope system using an image pickup device with a high number of pixels preferably satisfies the aforementioned expression:

$$2.4 \leq Fno/Pix \leq 4.5 \tag{5}$$

If Fno/Pix becomes smaller than 2.4 which is the lower limit of the range of expression (5), the effective F number Fno of the objective optical system 16 becomes too small to obtain a desired depth of field. Alternatively, although the depth of field is sufficient, the Pix size of an imager is large and the resolution decreases. Alternatively, when the number of pixels is increased, the resolution improves, but since the imager size increases, the size of the objective optical system 16 increases and if mounted on the distal end portion 6a of the endoscope 2, its outside diameter increases, which is undesirable (because insertability deteriorates).

On the contrary, if Fno/Pix increases beyond the upper limit of the range of expression (5), the effective F number Fno of the objective optical system becomes too large to obtain desired brightness.

At the same time, since Fno/Pix by far exceeds the diffraction limit or it is not a reasonable interpolation scheme, the resolution deteriorates.

In the setting shown in the aforementioned table in FIG. 6 of the present embodiment, the image pickup unit 19 is complementary color-based and of a simultaneous type, and, it is a common practice to set the coefficient k1 to on the order of 3 in this case. Furthermore, using a complementary color-based, simultaneous image pickup device having a pixel size of 1.7 μm, if the margin coefficient k2 from the diffraction limit F number of the objective optical system 16 is assumed to be k2=1, the following equation is derived from equation (12):

$$Fno/\text{Pix}=4.5 \tag{13}$$

The endoscope system 1 in such a configuration includes the objective optical system 16 as an endoscope objective optical system to obtain two optical images having different focus positions for the same object, the two image pickup devices 17a and 17b that receive and photoelectrically convert the two optical images having different focus positions, the image synthesis processing section 33 that synthesizes two images corresponding to the two optical images from the two image pickup devices 17a and 17b into one image, and the actuator 22 that moves the position of the focus lens 21 as a focus switchover lens provided in the endoscope objective optical system and constitutes a focus switchover mechanism for selectively switching focus of the endoscope objective optical system to one of two observation regions of proximity observation and remote observation, in which the image synthesis processing section 33 synthesizes the two images in each of the respective observation regions of the proximity observation and the remote observation.

Next, operation of the present embodiment will be described. Operation of the present embodiment in a case where an operator as a user performs an endoscope inspection of the interior of the body cavity using the endoscope 2 will be described below.

As shown in FIG. 1, after connecting the endoscope 2 and the light source apparatus 3 to the processor apparatus 4, the operator turns ON the power.

Figure 4B:
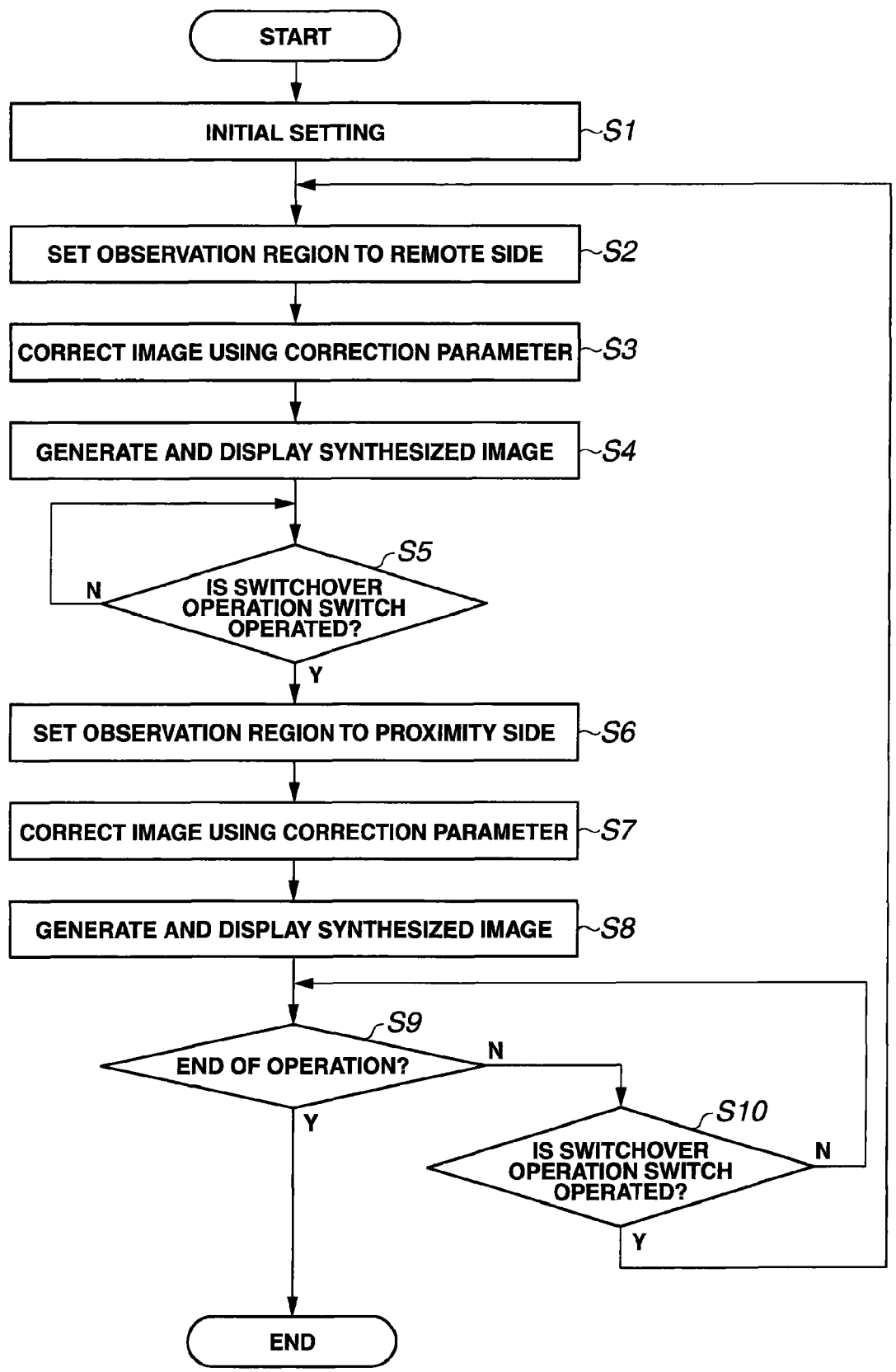
FIG. 4B is a flowchart illustrating operation contents of the first embodiment.

As an initial setting in first step S1 in FIG. 4B, the control section 39 performs control of setting a remote side as an observation region. The control section 39 assumes that the switchover operation switch 26 in this initial setting state is set to output a signal indicating that the remote side is an observation region to the control section 39.

In correspondence with this initial setting, as shown in step S2, the control section 39 drives the focus lens 21 via the actuator control section 25 and the actuator 22 to set a state in which focus is on the far point side so that the objective optical system 16 sets the remote side as the observation region.

Furthermore, in this case, as shown in step S3, the image correction processing section 32 corrects the two images of the two image pickup devices 17a and 17b using correction parameters.

Furthermore, as shown in step S4, the image synthesis processing section 33 generates a synthesized image for the two images corrected by this image correction processing section 32, outputs the synthesized image to the image display apparatus 5 side, and the image display apparatus 5 displays the synthesized image.

FIG. 5(A) illustrates a state corresponding to step S2 in which the image pickup unit 19 picks up an image.

FIG. 5(A) illustrates a situation in which the objective optical system 16 forms images on the image pickup devices 17a and 17b in a state in which the focus lens 21 is set so that the focus of the objective optical system 16 is on a remote observation region.

FIG. 5(A) shows the objective optical system 16 corresponding to a state in which the focus lens 21 is set at (switched to) the position Pa on the front side, the prism 18 that separates the image into two optical images is arranged on the image forming side, the image pickup devices 17a and 17b attached to their respective end faces receive the two optical images and output the respective photoelectrically converted signals.

In this remote observation state, the depth of field is expanded as follows using the synthesized image obtained from the two image pickup devices 17a and 17b.

As described above, optical path lengths to the image pickup devices 17a and 17b in the prism 18 are different from each other and the image pickup devices 17a and 17b acquire images with relatively different focus positions.

For example, an image focused on the (remote) far point side is formed on the image pickup device 17b and an image focused on the proximity side relatively more than the image pickup device 17b is formed on the image pickup device 17a.

Assuming the depth of field in the image pickup device 17a is Xaf, and the depth of field in the image pickup device 17b is Xbf in this remote observation region, the (objective optical system 16 and the image pickup devices 17a and 17b of the) image pickup unit 19 is set so that the end of depth of field on the near point side of the depth of field Xbf overlaps the end of depth of field on the far point side of the depth of field Xaf.

When the depth of field described in FIG. 3 is applied, the depths of field corresponding to the images formed on the image pickup devices 17a and 17b are Xaf and Xbf respectively as shown in FIG. 5(A).

Furthermore, when the images are synthesized through the image synthesis processing by the image synthesis processing section 33 shown in FIG. 1 and FIG. 4A, if the depth of field corresponding to the case of the synthesized image focused on remote observation is assumed as a combined depth of field, Xaf+Xbf can be obtained as the combined depth of field. However, in the overlapping portion (region with a small contrast difference), one combined depth of field is obtained through synthesized image processing of assigning predetermined weights to the respective images and adding up the weighted images. That is, Xaf+Xbf (6.54 mm to 128.59 mm) is obtained as the combined depth of field.

Particularly, when performing screening while looking down a wide range as described above in an endoscope inspection, if such a wide combined depth of field Xaf+Xbf is obtained, the endoscope inspection can be smoothly performed.

By contrast, when it is only a narrow depth of field that can be obtained, for example, a near point side portion may be unclear in an image obtained during screening, making it difficult to smoothly perform an endoscope inspection.

As shown in step S5 in FIG. 4B, the control section 39 monitors whether or not the operator operates the switchover operation switch 26, and if the operator does not operate the switchover operation switch 26, the control section 39 moves back to the process in step S5.

After ending the screening, if the operator wants to perform a diagnosis at a shorter distance, the operator operates the switchover operation switch 26.

If the switchover operation switch 26 is operated, the control section 39 moves to a process in step S6. In step S6, the control section 39 performs control of setting the observation region to proximity side. The control section 39 drives the focus lens 21 via the actuator control section 25 and the actuator 22 to set the objective optical system 16 in a state in which focus is on the near point side so that the objective optical system 16 sets the proximity side as the observation region.

Furthermore, in this case, as shown in step S7, the image correction processing section 32 corrects the two images from the two image pickup devices 17a and 17b using correction parameters. However, if there is no significant difference in the correction amount in step S6 compared to step S2, the same parameters may be used and new correction need not be performed. Next, as shown in step S8, the image synthesis processing section 33 generates a synthesized image by synthesizing the two images corrected by the image correction processing section 32, outputs the synthesized image to the image display apparatus 5 side and the image display apparatus 5 displays the synthesized image.

FIG. 5(B) illustrates an image pickup state by the image pickup unit 19 which corresponds to step S6.

FIG. 5(B) is a diagram illustrating a state in which focus is on an observation region where the focus lens 21 is set at (switched to) the position Pb on the rear side to perform proximity observation in FIG. 5(A).

In this state of proximity observation, the depth of field can be expanded as in the case of FIG. 5(A), using the synthesized image obtained from the two image pickup devices 17a and 17b as follows.

Assuming the depth of field in the image pickup device 17a is Xan and the depth of field in the image pickup device 17b is Xbn, the (objective optical system 16 and the image pickup devices 17a and 17b of the) image pickup unit 19 is set so that the end of depth of field on the near point side of the depth of field Xbn overlaps with the end of depth of field on the far point side of the depth of field Xan.

Furthermore, when images are synthesized through the image synthesis processing by the image synthesis processing section 33 in FIG. 1, if the depth of field corresponding to the case of the synthesized image in a state in which focus is on the observation region of proximity observation is assumed to be a combined depth of field, Xan+Xbn can be obtained as the combined depth of field.

Particularly when details of a lesion are observed or diagnosed in an endoscope inspection, a proximity observation state is set in which observation is performed in proximity to the lesion.

The present embodiment can obtain the wide combined depth of field Xan+Xbn while maintaining high resolution, and can thereby clearly observe details of a lesion and smoothly perform a diagnosis.

Furthermore, as shown in FIG. 5(A) and FIG. 5(B), the present embodiment sets the (range of) combined depth of field Xaf+Xbf in the case of remote observation and the (range of) combined depth of field Xan+Xbn in the case of proximity observation so as to overlap with each other. Thus, when a remote observation state and a proximity observation state are switched from one to the other, the present embodiment allows observation without producing any observation region where images become unclear (blurred) at some midpoint between both observation states, and thereby allows the operator to smoothly perform an endoscope inspection.

As described in the above configuration, and FIG. 4B and FIG. 5, the present embodiment can expand the depth of field without deteriorating resolution even when using an image pickup device with an increased number of pixels. Furthermore, the present embodiment provides the focus switchover mechanism or the focusing mechanism, and can thereby smoothly perform observation or diagnosis for an endoscope inspection by switching the observation range and using high image quality endoscope images.

In FIG. 4B, in step S9 after step S8, the control section 39 determines whether or not an instruction for ending the endoscope inspection is given and ends the endoscope inspection when an instruction for ending the endoscope inspection is given, or when an instruction for ending the endoscope inspection is not given, the control section 39 determines in next step S10 whether or not the switchover operation switch 26 is operated.

When the switchover operation switch 26 is not operated, the control section 39 continues the process in step S10, and when the switchover operation switch 26 is operated, the control section 39 returns to step S2, sets the observation region to the remote side and repeats the aforementioned operation.

According to the present embodiment that performs such an operation, the depth of field can be expanded no matter which of the observation region on the remote side or the observation region on the proximity side is set.

Furthermore, the present embodiment can provide an endoscope system which is applicable (that is, mountable at the distal end portion 6a of the insertion portion 6 of the endoscope 2) to an endoscope that performs proximity observation and remote observation, and can satisfy the depths of field necessary for proximity observation and remote observation respectively.

Furthermore, by making a setting so as to satisfy aforementioned expression (5), it is possible to obtain a desired depth of field, realize a small-sized system mountable at the distal end portion 6a of the endoscope 2, secure desired brightness and prevent deterioration of resolution.

Note that the objective optical system 16 to acquire two optical images having different focus positions may be set to be telecentric in which a principal light beam becomes parallel to the optical axis (or a diaphragm is arranged at the position of the rear side focus of the objective optical system 16).

If the objective optical system 16 is telecentric, no magnification difference dependent on the focus position occurs, which eliminates the necessity for correction through image processing and can simplify an image processing algorithm for generating a synthesized image, which is desirable.

When downsizing of the objective optical system 16 mounted at the distal end portion 6a of the insertion portion 6 of the endoscope 2 is aimed, the telecentricity of the objective optical system 16 may be lost. However, if the angle of incidence upon the image pickup surfaces of the image pickup devices 17a and 17b is too large, the magnification difference dependent on the focus position increases, the amount of correction by the aforementioned image correction processing increases and image quality degrades, which is undesirable.

Thus, the objective optical system 16 that acquires two optical images with different focus positions preferably sets the angle of incidence of light which forms images on the image pickup surfaces of the image pickup devices 17a and 17b to less than 10 degrees. Note that the aforementioned embodiment shown in FIG. 2 or the like uses the prism 18 using the right triangular prism shaped prism elements 18a and 18b as optical elements for separating an image into two images, but a configuration shown in FIG. 7 may also be used.

Figure 7:
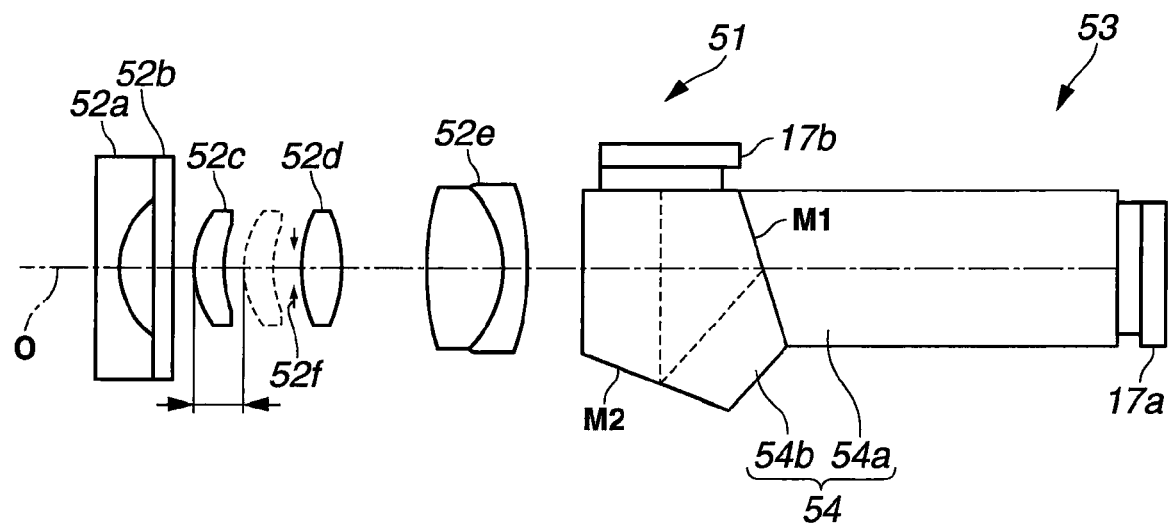
FIG. 7 is a diagram illustrating a configuration of an image pickup unit according to a modification of the first embodiment.

A prism 54 that constitutes an objective optical system 51 in FIG. 7 is constructed of a first prism 54a mounted with an image pickup device 17a that receives transmitted light and a second prism 54b mounted with an image pickup device 17b that receives reflected light. This objective optical system 51 and the image pickup devices 17a and 17b constitute an image pickup unit 53.

Furthermore, the objective optical system 51 except the prism 54 in this case is provided with optical elements 52a to 52f and an optical element 52c constitutes a focus lens 21. Note that a brightness diaphragm 52f is arranged between the optical elements 52c and 52d.

In the objective optical system 51 shown in FIG. 7, a joint surface M1 of the second prism 54b formed of a pentaprism facing the first prism 54a is (mirror) coated with a dielectric film that functions as a half mirror.

Light incident along an optical axis O of the objective optical system 51 passes by approximately half (50%) through the joint surface, forms an optical image on the image pickup surface of the image pickup device 17a, with the remaining approximately half being reflected one time, then reflected for the second time on a reflection surface of an end face M2 on the reflected light side which is (mirror) coated with a dielectric film for total reflection, then received by the image pickup device 17b attached to an end face facing this reflected light. The coating of the end face M2 may be metal coating of Al—SiO2 or Ag—SiO2 or the like.

In this case, the light is reflected two times, that is, an even number of times, until an optical image is formed on the image pickup device 17b via the objective optical system 51, and therefore the image formed is not a mirror image, and the processor apparatus 4 is not required to perform image processing for inverting the mirror image.

Thus, since the image processing for inverting the mirror image is unnecessary, the processing becomes simpler and degradation of image quality caused by the inversion image processing does not occur. However, when an analog image is converted to a digital image and temporarily stored in a memory, an inverted image can be easily generated by changing the address when reading from the memory, and in such a case, substantially no degradation of image quality occurs.

Note that in the case of the aforementioned prism 18 in FIG. 2, since an optical image is formed on the image pickup device 17b after one reflection, that is, an odd number of reflections, the image formed is a mirror image and the processor apparatus 4 applies image processing of inverting the mirror image.

Correction of the mirror image through an even number of optical reflections may result in an increase in the size of the objective optical system or an increase in the prism cost, and therefore correction of the mirror image through an odd number of reflections in FIG. 2 may be performed by the image correction processing section 32 through mirror image inversion.

It is a matter of course that the configuration in which light is optically reflected an even number of times as shown in FIG. 7 may also be adopted as long as there is no problem with upsizing of the objective optical system 16 or cost increase.

Next, second to sixth embodiments using image pickup devices or the like which are different from those in the aforementioned embodiment will be described one by one.

(Second Embodiment)

An endoscope system according to a second embodiment is a frame-sequential type endoscope system, which gives priority to brightness, as will be understandable from the following numerical value data, and adopts a configuration capable of acquiring a bright image.

Figure 8:
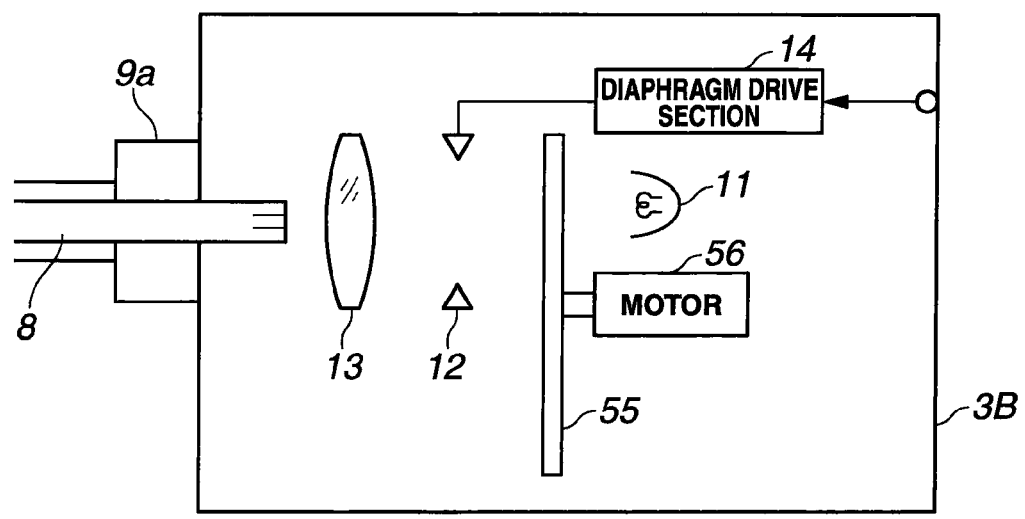
FIG. 8 is a diagram illustrating a configuration of a light source apparatus according to a second embodiment of the present invention.

The present endoscope system adopts a light source apparatus 3B that generates frame-sequential illuminating light as shown in FIG. 8 for the light source apparatus of the endoscope system 1 in FIG. 1. The light source apparatus 3B in FIG. 8 corresponds to the light source apparatus 3 in FIG. 1 in which a rotation filter 55 is arranged in the illuminating optical path between the lamp 11 and the diaphragm 12 and this rotation filter 55 is rotated by a motor 56.

In the rotation filter 55, R, G and B filters are provided in a fan shape to selectively allow red (R), green (G) and blue (B) light to pass therethrough respectively and can supply R, G and B frame-sequential illuminating light to the light guide 8 by further allowing light to pass through the rotation filter 55 in the configuration in FIG. 1.

Furthermore, in this case, for example, the image reading section 31 of the processor apparatus 4 in FIG. 1 is provided with a frame memory that temporarily stores frame-sequentially read images and reads the images simultaneously to thereby generate synchronized color images.

Furthermore, although the first embodiment uses the image pickup device provided with a simultaneous, that is, color separation filter, the image pickup device that constitutes the image pickup unit mounted at the distal end portion 6a of the insertion portion 6 of the endoscope 2 according to the present embodiment adopts two monochrome image pickup devices 61a and 61b.

As the numerical value data of the image pickup unit in this case, for light having wavelength $\lambda=0.5461$ µm, pixel size Pix in the vertical direction of the two image pickup devices 61a and 61b is set to 1.45 µm, resolution coefficient k1 is set to 2.00 and F value margin k2 is set to 0.80, and effective F number Fno of the objective optical system is set to 3.48 as correction parameters. The present embodiment has a feature of adopting a frame-sequential scheme using a monochrome image pickup device with 0.86 million pixels, each pixel being 1.45 µm in size, providing more allowable margin for the diffraction limit Fno and having a setting with greater emphasis placed on brightness.

In the image pickup unit of the present embodiment, Fno/Pix=2.40.

More detailed numerical value data is shown in the table in FIG. 6. Note that the table in FIG. 6(A) shows data also including the case of an embodiment giving priority to brightness that satisfies $2.4 \leq Fno/Pix \leq 4.5$—the condition in aforementioned expression (5). Furthermore, the table in FIG. 6(B) shows data in the case of an embodiment (embodiment 2') with emphasis placed on expansion of the depth of field that satisfies $2.7 \leq Fno/Pix \leq 4.5$—the condition in expression (5)' which will be described later. Furthermore, the table in FIG. 6(C) shows data in the case of an embodiment that limits a simultaneous scheme of primary color Bayer that satisfies $3 \leq Fno/Pix \leq 4.2$ (more strictly $2.97 \leq Fno/Pix \leq 4.2$)—the condition of expression (5)" which will be described later and within a lower limit range narrowed down to expansion of the depth of field.

The present embodiment is likewise applicable to a case with a frame-sequential scheme and has effects similar to those of the first embodiment.

That is, according to the present embodiment, the depth of field can be expanded no matter which of the observation region on the remote side or the observation region on the proximity side is set.

Furthermore, the present embodiment can provide an endoscope system which is applicable (that is, mountable at the distal end portion 6a of the insertion portion 6 of the endoscope 2) to an endoscope that performs proximity observation and remote observation, and can satisfy the depths of field necessary for proximity observation and remote observation respectively.

Third to sixth embodiments described below will also have effects substantially similar to those of the first embodiment.

(Third Embodiment)

As in the case of the first embodiment, an endoscope system according to the present embodiment is a simultaneous endoscope system. While the first embodiment adopts complementary color-based color separation filters as the two image pickup devices 17a and 17b of the image pickup unit 19, the present embodiment adopts a primary color separation filter. The endoscope of this embodiment has a feature of using a primary color Bayer array simultaneous image pickup device with 1.5 million pixels, each pixel being 1.1 μm in size, and having an ultra-high number of pixels of relatively small size (micropixels having small image pickup size). The present embodiment can provide an endoscope image, which has a narrower width of depth of field in absolute value compared to the first and second embodiments, yet has a smaller diameter and high image quality while keeping the practical depth of field.

As numerical value data of the image pickup unit in this case, for light of wavelength $\lambda$=0.5461 μm, pixel size Pix in the vertical direction of the two image pickup devices is set to 1.1 μm, resolution coefficient k1 is set to 2.80 and F value margin k2 is set to 1.0, and effective F number Fno of the objective optical system is set to 4.62 as correction parameters.

The image pickup unit of the present embodiment is Fno/Pix=4.20.

More detailed numerical value data is shown in the table in FIG. 6.

The present embodiment has effects similar to those of the first embodiment.

(Fourth Embodiment)

An endoscope system of the present embodiment corresponds to a modification of the third embodiment. The endoscope system of the present embodiment has 1.5 million pixels like the third embodiment, but adopts a large opening by setting a pixel size of 1.45 μm for the image pickup device, and has a setting in consideration of relatively greater allowance for noise or brightness. In this case, by further optimizing the interpolation method in a primary color Bayer array, it is possible to obtain a great depth of field as a synthesized image while preventing the resolution from deteriorating compared to the third embodiment.

As numerical value data of the image pickup unit in this case, for light of wavelength $\lambda$=0.5461 μm, pixel size Pix in the vertical direction of the two image pickup devices is set to 1.45 μm, resolution coefficient k1 is set to 2.80 and F value margin k2 is set to 1.0, and effective F number Fno of the objective optical system is set to 6.09 as correction parameters.

The image pickup unit of the present embodiment is Fno/Pix=4.20.

More detailed numerical value data is shown in the table in FIG. 6.

The present embodiment has effects similar to those of the first embodiment.

(Fifth Embodiment)

An endoscope system of the present embodiment corresponds to a modification of the third embodiment. The endoscope system according to the present embodiment uses a simultaneous image pickup device of a primary color Bayer array with 1.2 million pixels, each pixel being 1.1 μm in size and aims to have a relatively high-number of pixels of smaller size than the third embodiment. Furthermore, the present embodiment is an embodiment that narrows down the aperture more and gives higher priority to the depth of field than the resolution, and although the resolution deteriorates to a certain degree beyond the diffraction limit Fno, the present embodiment sets such a depth of field as to enable the observation distance to be reduced down to 3 mm so as to allow the proximity observation side to move closer and perform expanded observation while keeping a practical level thereof. Furthermore, such a combined depth of field is obtained that the observation distance is reduced by giving priority to expanded observation, yet a width of depth of field of 3 mm is secured, causing no trouble for an endoscope inspection.

As the numerical value data of the image pickup unit in this case, for light having wavelength $\lambda$=0.5461 μm, pixel size Pix in the vertical direction of the two image pickup devices is set to 1.10 μm, resolution coefficient k1 is set to 2.80 and F value margin k2 is set to 1.0, and effective F number Fno of the objective optical system is set to 4.62 as correction parameters.

In the image pickup unit of the present embodiment, Fno/Pix=4.20.

More detailed numerical value data is shown in the table in FIG. 6.

The present embodiment has effects similar to those of the first embodiment.

(Sixth Embodiment)

An endoscope system of the present embodiment corresponds to a modification of the third embodiment. The endoscope system according to the present embodiment uses a simultaneous image pickup device of a primary color Bayer array with 1.0 million pixels, each pixel being 1.7 μm in size and aims to obtain a wide depth of field for a synthesized image while giving higher priority to brightness during observation than the depth of field.

As the numerical value data of the image pickup unit in this case, for light having wavelength $\lambda$=0.5461 μm, pixel size Pix in the vertical direction of the two image pickup devices is set to 1.70 μm, resolution coefficient k1 is set to 2.80 and F value margin k2 is set to 1.0, and effective F number Fno of the objective optical system is set to 7.14 as correction parameters.

In the image pickup unit of the present embodiment, Fno/Pix=4.20.

More detailed numerical value data is shown in the table in FIG. 6.

The present embodiment has effects similar to those of the first embodiment.

Since it is generally more difficult to secure a depth of field as the pixel size of an image pickup device decreases, it tends to be more difficult to take a smaller k2 and provide allowance for brightness as in the case of the aforementioned second embodiment.

In this case, as the possible range of k2, 0.9 to 1.0 is considered to be practical on the premise that it will not exceed the diffraction limit Fno. For example, according to the second embodiment that provides a certain degree of allowance for the setting of brightness of the observation system, if k2 is assumed to be 0.9, Fno/Pix=2.7. According to the embodiment of the present application, the upper limit value corresponds to the first embodiment. Therefore, when a device with high number of pixels is aimed and more emphasis is placed on securing the depth of field rather than brightness of the observation system, Fno/Pix may be:

$$2.7 \leq Fno/\text{Pix} \leq 4.5 \qquad (5)'$$

(see lower limit data in (5)' according to embodiment 2' of the table in FIG. 6(B) and upper limit data in (5)' according to the first embodiment). In this case, though a sufficient combined depth of field is obtained, if brightness is insufficient, various improvements may be made such as adopting a back side illumination CMOS sensor for the image pickup device, optimizing a noise reduction function (not shown) of the processor apparatus 4 so as to multiply the brightness by a greater gain. Furthermore, if there is sufficient allowance in the diameter of the distal end of the endoscope, the number of light guides may be increased to supplement the total brightness.

Furthermore, as represented by the back side illumination CMOS sensor, from requirements such as an increase in the number of pixels accompanying the miniaturization of pixels, low power consumption and cost reduction, there may be a growing number of cases in the future where a CMOS sensor will be adopted for an image pickup device of an endoscope. In the case of a general CMOS sensor of a primary color Bayer array, as described above, resolution comparable to that of a frame-sequential scheme can be expected through optimization of the interpolation scheme (on the order of $k1=2.2$).

On the other hand, regarding the miniaturization of pixels, which may however cause deterioration of S/N or the like, a CMOS of a smaller cell size may be selected for a diameter reduction and size reduction for the endoscope whose diameter is preferably small. In such a case, even if the interpolation method is optimized, a certain degree of deterioration of resolution is assumed as a consequence, and the arbitrary coefficient k1 can be smaller than that of the complementary color scheme, but k1 may be on the order of 2.8. That is, in the case of a CMOS sensor of a primary color Bayer array, k1 may practically be on the order of $2.2 \leq k1 \leq 2.8$.

As described above, in the case where $k2=0.9$ to 1.0 and $k1=2.2$ to 2.8 with emphasis placed on the depth of field, this is applicable to the third to sixth embodiments that presuppose the use of a CMOS sensor of a primary color Bayer array among the embodiments of the present application, and expression (5)' then becomes:

$$2.97 \leq Fno/\text{Pix} \leq 4.2 \qquad (5)''$$

Therefore, when a CMOS sensor of a primary color Bayer array is adopted for the image pickup device with emphasis placed on the depth of field, a sufficient depth of field can be obtained even when expression (5)" is employed (see lower limit data in (5)" according to the fourth embodiment in the table in FIG. 6(C) and upper limit data in (5)" according to embodiment 3").

As described above, when a combined depth of field of two images with different focus positions is obtained, it is preferable that MTF at the respective ends of depths of field be equal to or greater than 10% and also the respective ends of depths of field overlap each other. As described above, if an evaluation spatial frequency on the image surface is assumed to be Fi, $$Fi=1/k1 \cdot \text{Pix} \qquad (5)$$

If a defocus MTF at this Fi is approximately 10%, blur in the image cannot be recognized through experimental objective evaluation and can be determined "visible." In other words, an MTF of approximately 10% or above can be assumed to fall within the depth of field.

Figure 9:
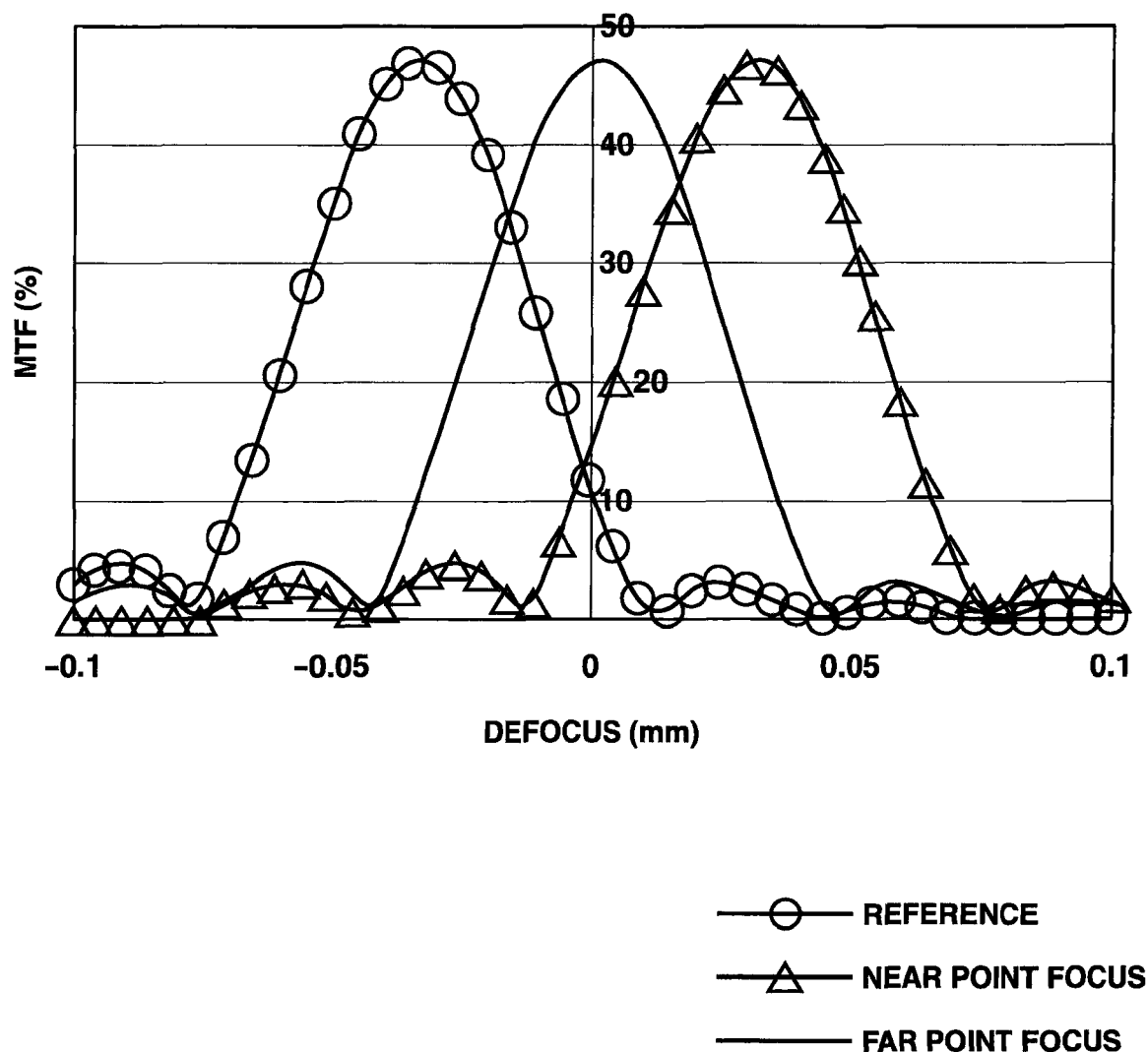
FIG. 9 is a diagram illustrating that two image pickup devices having different focus positions in remote observation and proximity observation are set such that their respective depths of field overlap each other within a range of the depth of field having an MTF of 10% or greater.

That is, when obtaining a combined depth of field in a two-focus state, the condition for the range of depth of field to become maximum is to realize the synthesis while keeping MTF to approximately 10% at the respective ends of depth of field. FIG. 9 shows this situation.

As indicated by Δ and ○ from reference MTF characteristics shown by solid lines in FIG. 9, when a setting is made so as to have MTF characteristics with focus positions shifted to the near point side and the far point side, in each of the aforementioned embodiments, overlapping is observed at ends of depth of field of the base where MTF is equal to or greater than 10% (both the combined depth of field on the remote observation side and the combined depth of field on the proximity observation side at the time of two-focus switchover).

Thus, a synthesized image synthesized in a state in which overlapping is observed at ends of depth of field of the base where MTF is equal to or greater than 10% has a desirable combined depth of field without any gap of depth of field being produced. Note that the aforementioned first to sixth embodiments satisfy this condition.

In contrast, if images are synthesized in a state at the ends of depth of field where MTF is less than 10%, an observation region may be generated which includes a gap portion of depth of field where MTF is less than 10% within the range of the combined depth of field, the observation region where images become unclear or blurred at that gap portion of depth of field.

Therefore, the aforementioned embodiment can provide an endoscope system that has a wide depth of field allowing a wide range to be clearly observed without producing any observation region where images become unclear even when two-focus switchover is performed.

Note that when the combined depth of field on the remote observation side and the combined depth of field on the proximity observation side at the time of two-focus switchover are set so that their respective ends of depth of field overlap each other (first to third and sixth embodiments), if remote observation is switched to proximity observation, it is possible to clearly observe images without producing any region where images become unclear between the both observations, and it is thereby easier to smoothly perform screening and detailed observation.

On the other hand, as in the cases of the fourth and fifth embodiments, a setting may also be made such that the combined depth of field on the remote observation side and the combined depth of field on the proximity observation side are not continuously connected and a gap of depth of field is produced (with N-F gap).

Such a setting makes it possible to realize a proximity and expanded observation, and thereby provide an endoscope that suits the purpose for a user who mainly uses a magnified endoscope.

However, it is desirable to secure a width of depth of field of approximately 3 mm in consideration of focusing with substantially no variation in the view angle at the time of two-focus switchover and the operability of the endoscope.

In the case where the view angle changes at the time of two-focus switchover, a variable power optical system may also be adopted whose observation magnification increases as it approaches an object.

In the aforementioned embodiment, the reference image pickup device may be set as an image pickup device whose focus is on the far point side. Such a setting has an effect of facilitating adjustment from a manufacturing perspective.

More specifically, a) in remote focusing, the image position is located closer to the object side than the image pickup surface (direction in which the image pickup device is pushed).

In contrast, b) in near point focusing, the image position is located closer to the user's hand side than the image pickup surface (direction in which the image pickup device is pulled). In focusing, a) may be preferably performed first, and then b).

If a) is performed after b) in focusing, the lenses may collide with each other at the time of focusing of the image pickup device on the far point side after b). In this case, focusing of b) must be performed again.

That is, it is possible to smoothly perform focusing by focusing the image pickup device on the near point side relative to the image pickup device on the far point side for which a focusing condition can be fixed through focusing first. Furthermore, in such a case, it is also possible to more smoothly perform image correction such as geometric correction (position, rotation) except magnification and brightness in addition to the focusing.

Note that a case has been described in the aforementioned embodiment where the objective optical system 16 or the like is set to perform two-focus switchover between a remote observation state and a proximity observation state by changing and setting the focus lens 21 at two positions in the optical axis direction, but the present invention is not limited to two-focus switchover, and it is possible to adopt a configuration that allows switchover among many foci (focus positions) such as 3 and 4 foci.

Furthermore, an embodiment configured by partially combining the aforementioned embodiments will also belong to the present invention.

What is claimed is:

1. An endoscope system comprising:
    an endoscope objective optical system that acquires two optical images with different focus positions from an identical object;
    an image pickup device that picks up the two optical images to acquire two image signals;
    an image synthesis processing section that makes a comparison in contrast between the two image signals for each spatially identical pixel region, and selects a pixel region having relatively higher contrast to thereby synthesize the two image signals into one image; and
    a focus switchover mechanism that moves a position of a focus switchover lens provided for the endoscope objective optical system and selectively switches a focus of the endoscope objective optical system to one of two observation regions of proximity observation and remote observation,
    wherein the image synthesis processing section synthesizes two images in each of the respective observation regions of the proximity observation and the remote observation.

2. The endoscope system according to claim 1, wherein the two optical images are picked up by two image pickup devices respectively.

3. The endoscope system according to claim 2, wherein the endoscope objective optical system and the two image pickup devices satisfy the following condition:

$$2.4 \leq Fno/\text{Pix} \leq 4.5$$

where an effective F number of the endoscope objective optical system is represented by Fno and a pixel pitch of pixels two-dimensionally arranged on image pickup surfaces of the two image pickup devices is represented by Pix.

4. The endoscope system according to claim 3, wherein the image pickup device comprises color filters of primary colors or complementary colors.

5. The endoscope system according to claim 3, wherein the image pickup device is a monochrome image pickup device having no color filter that picks up an image under frame-sequential illuminating light.

6. The endoscope system according to claim 3, wherein the image synthesis processing section comprises:
    a difference value calculation circuit that calculates a difference value between first and second luminance levels corresponding to identical object positions in first and second image data generated based on the two image pickup devices in each frame;
    a comparison circuit that makes a comparison to determine whether or not an absolute value of the difference value is equal to or greater than a threshold; and
    a selection circuit that selects an image with a higher luminance level when the absolute value of the difference value is equal to or greater than the threshold, or adds up luminance levels of two images and outputs the addition result when the absolute value of the difference value is less than the threshold.

7. The endoscope system according to claim 2, wherein the endoscope objective optical system that acquires the two optical images having different focus positions comprises an optical element that separates an image into two portions and is arranged between the two image pickup devices that receive the two optical images having different focus positions,
    the optical element that separates the image into two portions comprises a reflection surface that reflects at least one of the optical images one or more times, and
    the image reflected by the reflection surface is formed on one of the image pickup devices.

8. The endoscope system according to claim 2, further comprising an image correction processing section that performs image processing of canceling a relative magnification difference, a position difference, a rotation difference, and a brightness difference in the respective images from the two image pickup devices,
    wherein the image synthesis processing section synthesizes the respective images corrected by the image correction processing section into one image.

9. The endoscope system according to claim 8,
    wherein the image correction processing section reads a predetermined correction parameter from a correction parameter storage section and performs image correction, and
    a relative difference using one of the two optical images having different focus positions as a reference image is set in the correction parameter.

10. The endoscope system according to claim 9, wherein the endoscope system comprises the endoscope objective optical system, an endoscope comprising the two image pickup devices and an image processing apparatus to which the endoscope is detachably connected and which comprises the image synthesis processing section, and
    the endoscope comprises the correction parameter storage section.

11. The endoscope system according to claim 8, wherein the relative brightness difference corrected by the image correction processing section is corrected using one of the two images with lower luminance or one of the two images with lower luminance at a relatively identical position as a reference.

12. The endoscope system according to claim 8, wherein when reflections on the reflection surface of the optical element that separates the image into two portions are performed an odd number of times to form an image on one of the image pickup devices, the endoscope system comprises a function of inverting the image obtained from the one image pickup device as a mirror image.

13. The endoscope system according to claim 8, wherein the endoscope objective optical system is set so that in each of the respective observation regions of the proximity observation and the remote observation, a range of depth of field corresponding to one image pickup device of the two image pickup devices overlaps with a range of depth of field corresponding to the other image pickup device.

14. The endoscope system according to claim 13, wherein the image synthesis processing section comprises:
- a difference value calculation circuit that calculates a difference value between first and second luminance levels corresponding to identical object positions in first and second image data generated based on the two image pickup devices in each frame;
- a comparison circuit that makes a comparison to determine whether or not an absolute value of the difference value is equal to or greater than a threshold; and
- a selection circuit that selects an image with a higher luminance level when the absolute value of the difference value is equal to or greater than the threshold, or synthesizes two images after assigning respective weights to luminance levels thereof and outputs the synthesized image when the absolute value of the difference value is less than the threshold.

15. The endoscope system according to claim 2, wherein the endoscope objective optical system and the two image pickup devices satisfy the following condition:

$$2.7 \leq Fno/Pix \leq 4.5$$

where an effective F number of the endoscope objective optical system is represented by Fno and a pixel pitch of pixels two-dimensionally arranged on image pickup surfaces of the two image pickup devices is represented by Pix.

16. The endoscope system according to claim 2, wherein the endoscope objective optical system and the two image pickup devices satisfy the following condition:

$$3 \leq Fno/Pix \leq 4.2$$

where an effective F number of the endoscope objective optical system is represented by Fno and a pixel pitch of pixels two-dimensionally arranged on image pickup surfaces of the two image pickup devices is represented by Pix.

* * * * *